United States Patent [19]

Hodge

[11] Patent Number: 4,830,047
[45] Date of Patent: May 16, 1989

[54] CONTROL UNIT FOR INTERMITTENT SUCTION SYSTEM

[75] Inventor: Colin G. Hodge, Columbia, Md.

[73] Assignee: The BOC Group, Inc., Montvale, N.J.

[21] Appl. No.: 206,406

[22] Filed: Aug. 29, 1988

Related U.S. Application Data

[62] Division of Ser. No. 12,396, Feb. 9, 1987, Pat. No. 4,782,849.

[51] Int. Cl.⁴ .............................................. F16K 21/16
[52] U.S. Cl. ........................... 137/505.13; 137/624.11; 137/907
[58] Field of Search ...................... 137/624.11, 624.14, 137/505.13, 505.15, 907, 624.18, 103, 105, 624.2; 123/409

[56] References Cited

U.S. PATENT DOCUMENTS

| | | | |
|---|---|---|---|
| 2,345,379 | 3/1944 | Campbell | 137/624.14 X |
| 3,990,516 | 11/1976 | Christensen et al. | 137/624.11 X |
| 3,995,607 | 12/1976 | Ludwig et al. | 123/409 |
| 4,191,210 | 3/1980 | Belart et al. | 137/505.13 |
| 4,267,809 | 5/1981 | Mase et al. | 123/409 |
| 4,303,095 | 12/1981 | Aubel et al. | 137/907 X |
| 4,651,766 | 3/1987 | Ransom | 137/907 X |

Primary Examiner—Stephen Hepperle
Attorney, Agent, or Firm—Larry R. Cassett; Roger M. Rathbun

[57] ABSTRACT

An intermittent suction regulator is disclosed operating from a vacuum system and is used to provide a plurality of pneumatic output signals to a positive pulse device for returning fluids removed from a patient during drainage thereof to clear the removal passageways. The suction regulator or control unit provides two (2) timed output signals, from one (1) intermittent vacuum to atmospheric pressure input. One output signal continually switches from a regulated vacuum signal to an atmospheric pressure signal while the other output signal switches from providing an unregulated vacuum signal to an atmospheric pressure signal. The signals are timed such that both are initially set to provide vacuum signals simultaneously, however there is a predetermined time delay between the time the regulated vacuum output signal switches from vacuum to atmospheric and when the unregulated vacuum output signal switches from vacuum to atmospheric. Both output signals, however, again switch back to their vacuum signals simultaneously after a predetermined cycle time.

5 Claims, 4 Drawing Sheets

CONTROL UNIT FOR INTERMITTENT SUCTION SYSTEM

This is a division of application Ser. No. 012,396 filed Feb. 9, 1987 U.S. No. 4,782,849.

BACKGROUND OF THE INVENTION

This invention relates to a pneumatic timing device and, more particularly, to an intermittent suction regulator for providing various pulsed, timed signals to operate a positive pulse suction device.

Intermittent suction devices are used regularly to remove fluids from patients cavities, such as the stomach, and typically are utilized post-operatively to remove those fluids. Such devices operate typically from a main source of vacuum that is available in hospital recovery rooms by means of central piping systems.

In non-intermittent suction units, the hospital vacuum system withdraws the fluids continuously into some receiver and automatically discontinues the withdrawing cycle only when the collection container is full or hospital personnel disable the system.

With intermittent suction, the continuous withdrawing of fluids is intermittently, at timed intervals discontinued. In some units, the vacuum to the tubing withdrawing the fluids is cycled to atmospheric pressure so that a portion of the fluid moves backwardly toward the patient in order to clear obstructions in the line or to move the catheter away from the wall of the stomach. One difficulty with such systems is that the back flush is carried out to some extent by gravitational forces and therefore the collection container was placed higher than the patient, often incorporated into the timing apparatus itself on the hospital wall at the height of the receptacle providing the vacuum. In addition, gravity force often was not effective in that the tubing carrying fluid from the patient seldom contained a solid line of liquid but more often carried pockets of gas. A typical device of the type that returned the line withdrawing fluids to atmospheric pressure is shown and described in U.S. Pat. No. 3,659,605 of Ulrich Sielaff.

In an effort to correct some of the problems, positive pulse devices have been proposed and which send a positive quantity of fluid previously withdrawn from the patient, backwards toward the patient to clean the passageways. One of such devices is shown and described in U.S. Pat. No. 4,315,506 to Kayser et al.

While the normal suction/atmospheric cycle is sufficient to operate a device such as that of Kayser et al., it is advantageous to use other control systems, that provide more than one vacuum/atmospheric signal to the positive pulse suction device. By having more than one output signal from an intermittent suction regulator, one vacuum signal may be regulated in accordance with the desired vacuum to be applied to the patients cavity while the other vacuum signal may be uneffected by changes in the suction level to the patient and thus can independently control the timing of the positive pulse device. In addition, though the use of a control unit or suction regulator having two (2) output signals, one signal can be delayed or altered with respect to time with reference to the other signal.

BRIEF SUMMARY OF THE INVENTION

The present intermittent suction regulator or control unit thus may be powered entirely by the normal central vacuum system in a hospital and yet provides two (2) output signals, one of which is a regulated vacuum signal that continues to switch between regulated vacuum and atmospheric pressure similar to that of the Sielaff U.S. Pat. No. 3,659,605. This signal can be applied to the patient's cavity since the regulator can be set to the desired level of vacuum to be applied to the patient. A second signal is provided by the intermittent suction regulator that may be an unregulated vacuum and which cycles in synchronization with the regulated vacuum signal. The latter signal, however, is further provided with a unique pause valve means that introduces a predetermined time delay in its output switching to atmospheric upon it's input sensing a change from vacuum to atmospheric pressure. Thus, both vacuum signals are turned on simultaneously, however, when the first output delivering regulated vacuum to the patient is switched to atmospheric pressure, the other output signal representing unregulated vacuum is delayed momentarily before switching to its atmospheric pressure cycle. Thus, the vacuum from the first output signal is cycled to the patient and is regulated while the other output provides a vacuum signal that is also cycled with a time delay during one cycle change and which is used to operate the positive pulse suction device, thus, the latter signal can be used to operate the device while being isolated from the actual vacuum signal seen by the patient.

BRIEF DESCRIPTION OF THE DRAWINGS

The intermittent suction control unit is illustrated in the accompanying drawings which show the preferred embodiment of the invention incorporating the features and advantages described.

DESCRIPTION OF THE PREFERRED EMBODIMENT

Figure 1:
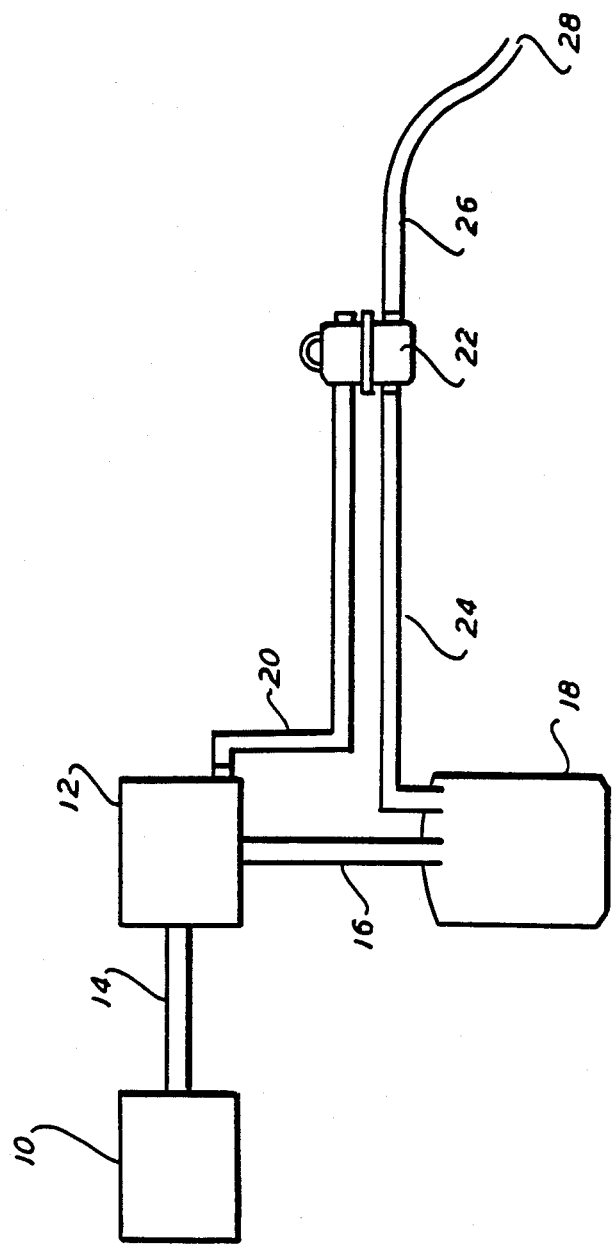
FIG. 1 is a flow diagram showing the control unit of the present invention installed to operate a positive pulse device attached to a catheter.

Referring now to FIG. 1, there is shown a flow diagram of a positive pulse suction system and having as a component; the new pause valve and intermittent suction control unit for removal of fluids from a patient.

A vacuum source 10 provides a regulated vacuum for operation of the suction system. Vacuum sources are relatively common in hospitals and provide a source of vacuum in certain individual hospital rooms from a central vacuum pumping system. The vacuum of such hospital systems typically may range within 300-600 mm Hg.

An intermittent suction control unit 12 of the present invention is connected to the vacuum source 10 by suitable connection means such as piping 14. The control unit 12 used in the present invention has one output shown as a regulated vacuum line 16 that leads to a collection container 18 and which receives the fluids drained from the patient. Control unit 12 has a second output shown as vacuum signal line 20 that goes directly into the positive pulse device 22 as will be explained.

Also connecting into the positive pulse device 22 is the regulated vacuum line 24 from control unit 12. A catheter 26 which is attached to the positive pulse device 22 and which is placed in the patient such that the open catheter end 28 reaches the fluids desired to be withdrawn. The passageways for fluid, regulated vacuum line 24 as well as vacuum signal line 20 and regulated vacuum line 16 may be standard relatively flexible medical tubing.

Figure 2:
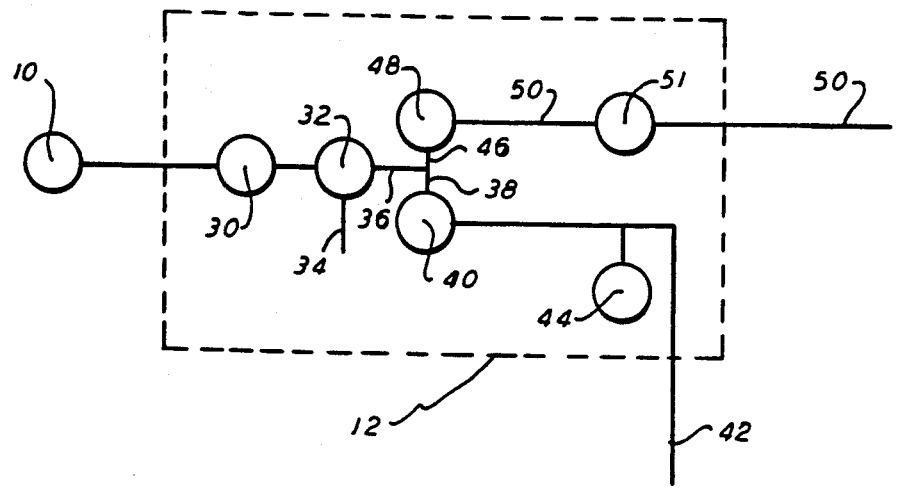
FIG. 2 is a flow diagram of the intermittent suction mechanism used with the present invention.

Turning now to FIG. 2, there is shown a flow diagram of the intermittent suction control unit 12 made in accordance with the present invention. The overall purpose of control unit 12 is to provide two (2) separate signal outputs, one being a regulated vacuum signal for ultimate use with the patient and the second signal, that need not be regulated acts as a vacuum signal for operating the positive pulse device. The present control unit 12 is pneumatically operated, however, the signals could be achieved by electronic switching or other means.

One of the important improvements between control unit 12 and the intermittent suction unit of the aforementioned Sielaff patient is that control unit 12 provides two (2) vacuum output signals at different timing cycles. In its operation, control unit 12 simultaneously supplies vacuum to two (2) outputs, one regulated and one that need not be regulated. During suction at the patient control unit 12 simultaneously supplies vacuum at both outputs and after the duration of the suction cycle, control unit 12 returns the regulated vacuum line, to the patient, to atmospheric pressure. After a predetermined short time interval the other vacuum output signal is returned to atmospheric pressure.

In FIG. 2, the vacuum source 10 provides the vacuum to control unit 12 as described previously with respect to FIG. 1. That source of vacuum is initially controlled by an "on-off" switch 30 which merely shuts off the vacuum from vacuum source 10 when the unit is not in use. A intermittent device 32 thereafter is controlled by the vacuum and may be of the same design as shown in the aforemention Sielaff U.S. Pat. No. 3,659,605. Intermittent device 32 includes an atmospheric vent 34 by which the further lines withdrawing fluids from the patient are intermittently vented to atmospheric pressure.

Tracing now, the source of vacuum that ultimately reaches the patient, the intermittent vacuum/atmospheric pressure signal from intermittent device 32 proceeds via passages 36 and 38 to a vacuum regulator 40 where the doctor, or other qualified personnel, actually sets the maximum level of vacuum that the patient can experience. The vacuum regulator 40 is conventional and thereafter the regulated vacuum proceeds by passage 42 to connect with regulated vacuum line 16 to collection container 18 (FIG. 1). A vacuum gauge 44 is in the passage 42 so that the doctor can verify and continually monitor that the regulated vacuum from control unit 12 is at the desired set point.

Returning to the intermittent device 32, the same intermittent vacuum/atmospheric pressure signal proceeds via passages 36 and 46 to a pause valve 48 where a predetermined time delay is created between the time that the signal from intermittent device 32 goes from vacuum to atmospheric pressure and the time that signal from the output of pause valve 48 to passage 50 goes from vacuum to atmospheric pressure, as will be latter explained. The passage 50 connects to vaccum signal line 20 of FIG. 1 and is used to control the positive pulse device 22. A liquid safety trap 51 is provided in passage 50 in order to prevent liquid from returning and entering pause valve 48.

The pause valve 48 is made and operated in accordance with the present invention.

Figure 3A:
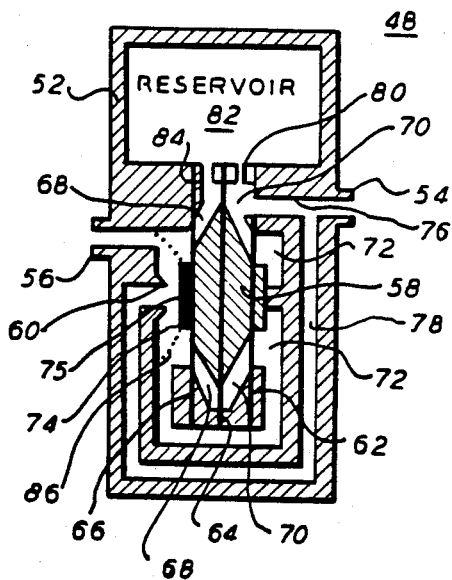
FIG. 3A is a cross-sectional view of the pause valve made in accordance with the present invention and used in the control unit of FIG. 2.
Figure 3B:
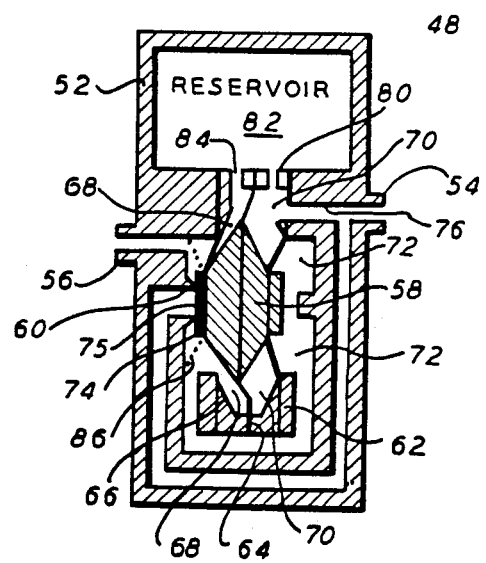
FIG. 3B is a cross-sectional view of the pause valve of FIG.3 A in its alternate position.

Turning now to FIGS. 3A and 3B, there is shown cross-sectional views of the pause valve 48. Pulse valve 48 comprises a housing 52, preferably of a plastic material having an inlet 54 which connects to passage 46 of FIG. 2 which is the intermittent vacuum/atmospheric pressure signal from the intermittent device (FIG. 2) and an outlet 56 which, in turn, connects to passage 50 of FIG. 2 and thereafter to the positive pulse device 22 (FIG. 1) and provides the vacuum signal therefore. Within housing 52 of pause valve 48 is a moveable valve member 58 and a valve seat 60. The moveable valve member 58 is retained within housing 52 by three diaphragms 62, 64 and 66 and which form various chambers in order that various levels of vacuum and/or atmospheric pressure influence the movement and position of moveable valve member 58. The diaphragms 62, 64 and 66 specifically divide the interior of the pause valve 48 into pilot chambers 68, 70 and main chambers 72 and 74.

Moveable valve member 58 additionally has a resilient pad 75 that seals against valve seat 60 when in the valve closed position of FIG. 3B. As shown in FIG. 3A, the moveable valve member 58 is in the valve open position and resilient pad 75 is not seated against valve seat 60.

Various passages are formed in housing 52, passage 76 communicates directly between inlet 54 and pilot chamber 70 while passage 78 is a longer passage than passage 76 and provides communication between inlet 54 and main chamber 74, the purpose of passage 78 being longer or having more resistance than passage 76 will become clear.

The pilot chambers 68 and 70 also are in communication between each other through a fixed orifice 80 which extends between pilot chamber 70 and reservoir 82 and by passage 84 between reservoir 82 and the other pilot chamber 68, otherwise pilot chambers 68 and 70 are isolated from each other by diaphragm 64. A spring 86 biases the moveable valve member 58 toward its valve open position as shown in FIG. 3A.

Taking now the operation of the pause valve 48, it should be reminded that the purpose thereof is to introduce a short delay between the time that the vacuum signal at its inlet 54 goes from vacuum to atmospheric pressure and the time that the vacuum signal at its outlet 56 goes to atmospheric pressure. As seen in FIG. 2, the delay occurs such that when the vacuum in passage 36 switches from vacuum to atmospheric pressure by the intermittent device 32, the regulated vacuum in passage 42 leading to the patient immediately also switches from vacuum to atmospheric while the signal in passage 50 is delayed slightly before it switches from vacuum to atmospheric pressure. Both signals, that in passage 36 and 42 are, however, controlled by intermittent device 32.

Returning to FIGS. 3A and 3B, the cycle can be commenced with all chambers, that is pilot chambers 68, 70 and main chambers 72 and 74 at atmospheric pressure and the valve is in the valve open position of FIG. 3A. As vacuum is applied to inlet 54 when the intermittent device 32 commences its vacuum or suction cycle, the vacuum immediately reaches pilot chamber 70, thereby reinforcing the bias of spring 86 and retaining the moveable valve member 58 in the position shown in FIG. 3A. The vacuum also communicates through passage 78 to draw a vacuum in main chambers 74 and 72. At this point, therefore, vacuum is drawn at outlet 56 and pilot chamber 70 as well as main chambers 74 and 72 so that all chambers expect pilot chamber 68 are at the high vacuum seen at the inlet 54. As time passes, the reservoir 82 is slowly evacuated through fixed orifice 80 such that over a predetermined time period, pilot chamber 68 also reaches high vacuum. At this point, all of the chambers 68, 70, 72 and 74 are at high vacuum.

As the intermittent device 32 switches to its atmospheric pressure mode, the pressure at inlet 54 immediately goes to atmospheric pressure and atmospheric pressure is simultaneously communicated to pilot chamber 70 through passage 76. Since the other chambers effecting surfaces of the moveable valve member 58 are balanced at high vacuum, the atmospheric pressure in pilot chamber 70 overcomes the force of spring 86 and moves the pause valve 48 to its position shown in FIG. 3B causing resilient pad 75 to close against valve seat 60. Since the passage 78 is relatively long and restricted, the valve seat 60 is closed by resilient pad 75 before atmospheric pressure can travel through passage 78 to reach main chamber 74. Thus, at this point in time, only the pilot chamber 70 and passages 76 and 78 are at atmospheric pressure while main chambers 72, 74 and the reservoir 82 are still at high vacuum.

Reservoir 82, however, slowly returns to atmospheric pressure by dissipation of its vacuum through atmospheric pressure entering through fixed orifice 80. As reservoir 82 returns to atmospheric pressure, so does pilot chamber 68. When pilot chamber 68 reaches atmospheric pressure, the pressure related forces on moveable valve member 58 become equal since both pilot chambers are at atmospheric pressure and the areas through which that atmospheric pressure acts upon moveable valve member 58 are equal. The main chamber 72 and 74 are both still at high vacuum and the respecrtive areas acting upon moveable valve member 58 are also equal, thus the only additional force acting upon moveable valve member 58 is the bias of spring 86 which is the resultant force and which moves the moveable valve member 58 but to its valve position position shown in FIG. 3A.

As the moveable valve member 58 moves to the FIG. 3A position, the passage through valve seat 60 also opens such that all chambers 68, 70, 72 and 74 are returned to atmospheric pressure and therefore the outlet 56 returns to atmospheric pressure. Thus a time delay is introduced between the time the inlet 54 is vented to atmospheric pressure and the time that atmospheric pressure appears as a signal at outlet 56.

Obviously, the actual pause time is a matter of design and depends upon the characteristics of spring 86, the volume of reservoir 82, the vacuum levels applied and the size of orifice 80.

Thus, in accordance with the present invention, a pause valve is described and which is usable in a unique intermittent suction control unit 12 used to control a positive pulse device by providing a plurality of vacuum and atmospheric pressure signals at predetermined timed intervals.

Turning now to FIGS. 4A-4D, there is shown a positive pulse device 22 that can be used with the signals of control unit 12 to withdraw fluids from a patient shown in its four (4) basic positions respectively, the VACUUM OFF, the VACUUM APPLIED mode, the VACUUM ON mode, and the REFLUX mode.

Taking FIG. 4 first, the positive pulse device 22 comprising a housing 88 which is conveniently made up of lower housing 90 and upper housing 92 which are joined together as will be explaned. Housing 88 has an inlet 94 which is connected to the collection chamber 18 (see FIG. 1) and therefore is connected to the source of regulated vacuum. An outlet 96 is also formed in housing 88 and is adapted to be connected directly or adjacent to a patient catheter. A value means is interposed between inlet 94 and outlet 96 and is formed by valve seat 98 and moveable valve member 100 that moves into engagement with valve seat 98 or away therefrom to control the flow between inlet 94 and outlet 96. Moveable valve member 100 has a truncated conical shape surface 102 that mates with valve seat 98 and which also forms an annular ridge 104 facing upwardly way from valve seat 98.

Moveable valve member 100 includes a valve extension 106 that depends upwardly and which is sonic welded to the lower part of moveable valve member. A spring bias is provided by a small spring 108 and which acts to bias the moveable valve member 100 toward its closed position against valve seat 98. This spring bias is very small, however, and is created by the preload effected by installing small spring 108 with lower end of small spring 108 seating on inner ledge 110 formed in the valve extension 106 and its upper end held by the lower end of moveable cap 112. Moveable cap 112, in turn, is biased toward valve extension 106 by medium spring 114 which acts against a flange 114 of moveable cap 112 having its other end seated against the top of housing 88. The moveable cap 112 is contained within a keeper 116 which retains the moveable cap 112 in position and limits its downward movement by an inner ledge 117. As noted in FIG. 4A, in the VACUUM OFF mode, the moveable cap 112 at its lowermost position does not directly touch the upper end of valve extension 106 in its lowermost position. Instead a gap 118 of about 0.040 inches is retained between the bottom of moveable cap 112 when it is in its lowermost position and the top of valve extension 106 when it is in its lowermost position. As will become clear, the spring constant of bias exerted by medium spring 114 is higher than that of small spring 108.

Figure 4A:
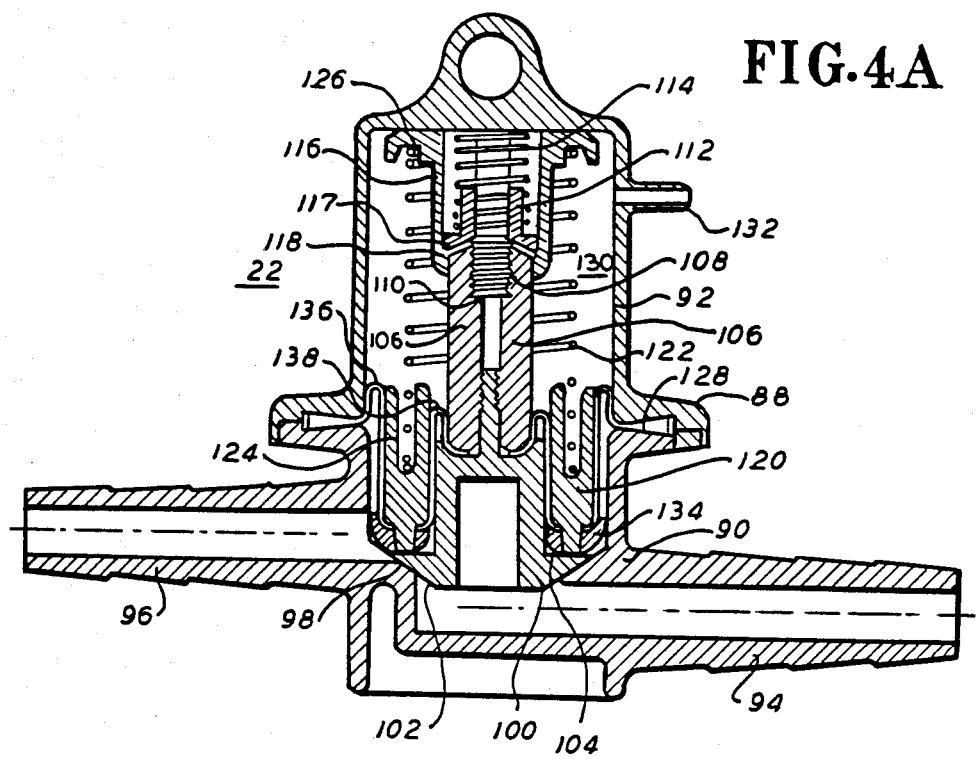
FIG. 4A is a cross-sectional view of a positive pulse device that is operable by means of the intermittent suction control unit of the present invention and shown in its VACUUM OFF mode.

Surrounding moveable valve member 100 is an annular piston 120 that moves independent of moveable valve member 100, however, in the position of FIG. 4A, annular piston 120 directly engages the annular ridge 104 of moveable valve member 100 and urges the moveable valve member 100 toward its closed position by the bias of large spring 122 which is precompressed and has its lower end held within annular groove 124 in annular piston 120 and its other end abuts against the top of housing 88 and held in position by spring keeper 126.

Thus, in the VACUUM OFF mode of FIG. 4A, the large spring 122 acts as an additional force in retaining the moveable valve member 100 in its closed position against valve seat 98.

A diaphragm 128 creates a control chamber 130 in the upper housing 92 and which control chamber 130 is sealed except for control port 132 which is adapted to be connected to vacuum signal line 20 (shown in FIG. 1). Diaphragm 128 has its outer peripheral edge secured in housing 88 by being sandwiched between lower housing 90 and upper housing 92 which may be sonic welded together. Diaphragm 128 has its inner edge sealed to moveable valve member 100 by the connection of the valve extension 106 to the lower part thereof, again which may be a sonic welded connection. Intermediate its outer periphery and its inner edge, diaphragm 128 is also sealed to annular piston 120, which seal may be effected by compressing the diaphragm 128 against annular piston 120 by means of annular gap 134 which also may be sonic welded to annular piston 120.

As shown, the diaphragm 128 is a single piece of flexible material, however, it may readily be made up of two (2) separate diaphragms while still carrying out the purpose of forming a pair of rolling seals, that is, an outer rolling seal at 136 and an inner rolling seal at 138. Each of the rolling seals 136 and 138 allow independent movement of moveable valve member 100 and annular piston 120 with respect to each other and yet retain the integrity of the control chamber 130.

Referring now to FIG. 1 as well as FIGS. 4A–4D, the operation of the positive pulse device 22 can be readily understood. Initially, at start-up, the positive pulse device 22 is in the position as shown in FIG. 4A. At this point in the cycle, the inlet 94, outlet 96 and the control part 32 are all at atmospheric pressure. The valve means is closed since moveable valve member 100 is in its lowermost position sealed against valve seat 98, so there is no communication between the inlet 94 and outlet 96. The moveable valve member 100 is retained in that position, being held there by the annular piston 120 acting against annular ridge 104 and biased by large spring 122 and by the bias of the small spring 108. Both large spring 122 and small spring 108 are, of course, preloaded. The catheter 26, and therefore outlet 96 may, at times, be slightly above atmospheric pressure due to positive tissue pressure in the stomach, however any drainage that might occur due to gravity or differential pressure forces is prevented by the closed valve means.

Figure 4B:
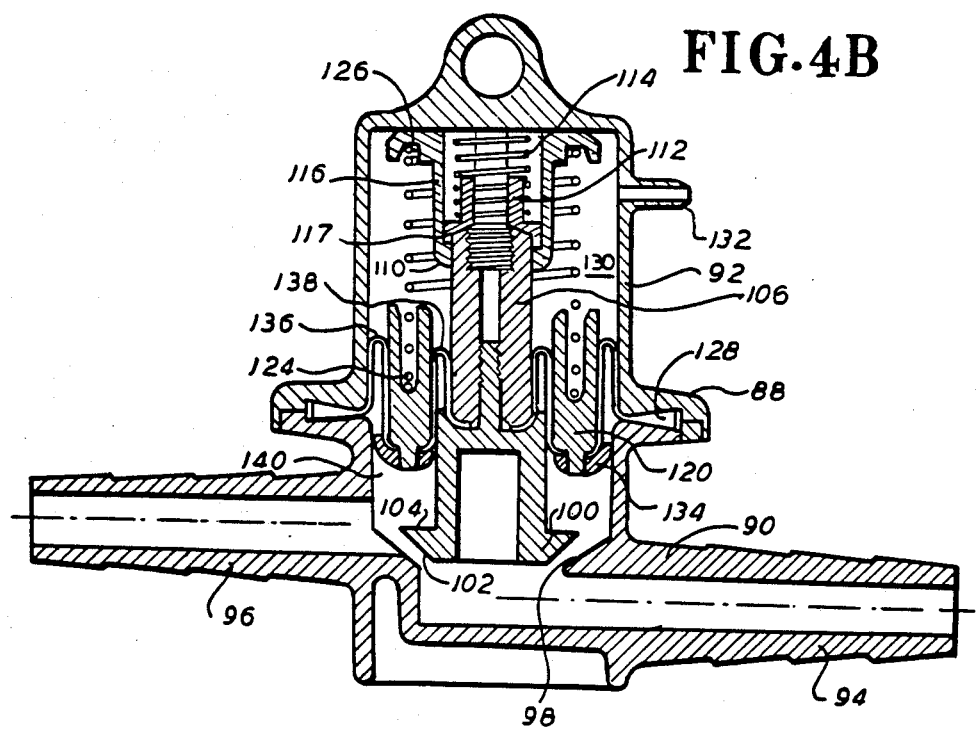
FIG. 4B is a cross-sectional view of the positive pulse device, of FIG. 4A shown in the VACUUM APPLIED mode.
Figure 4C:
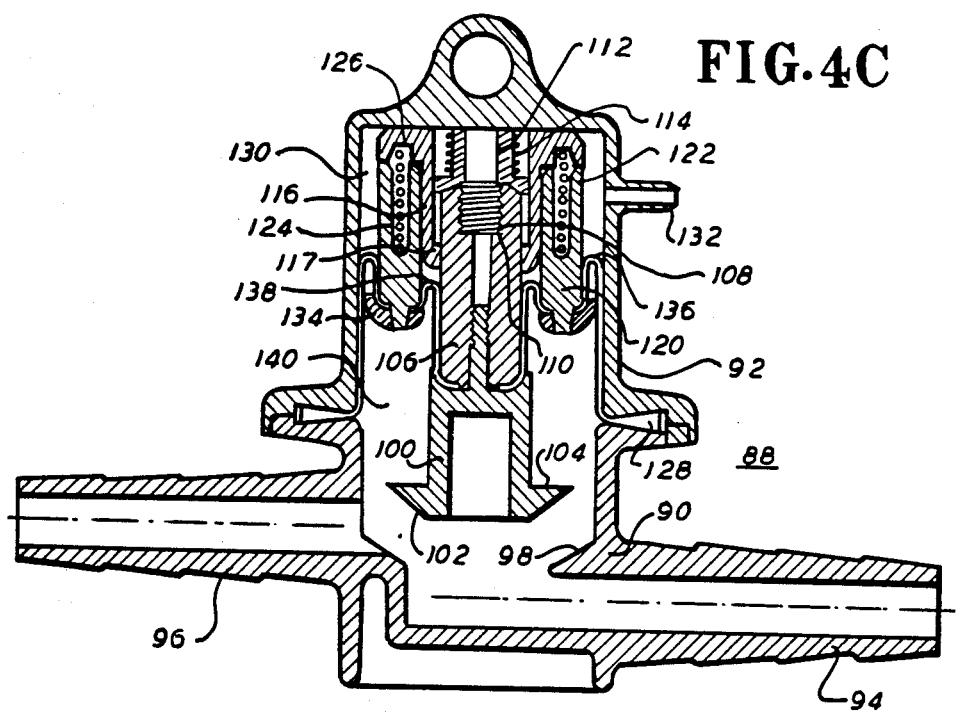
FIG. 4C is a cross-sectional view of the positive pulse device of FIG. 4A shown in the VACUUM ON mode.
Figure 4D:
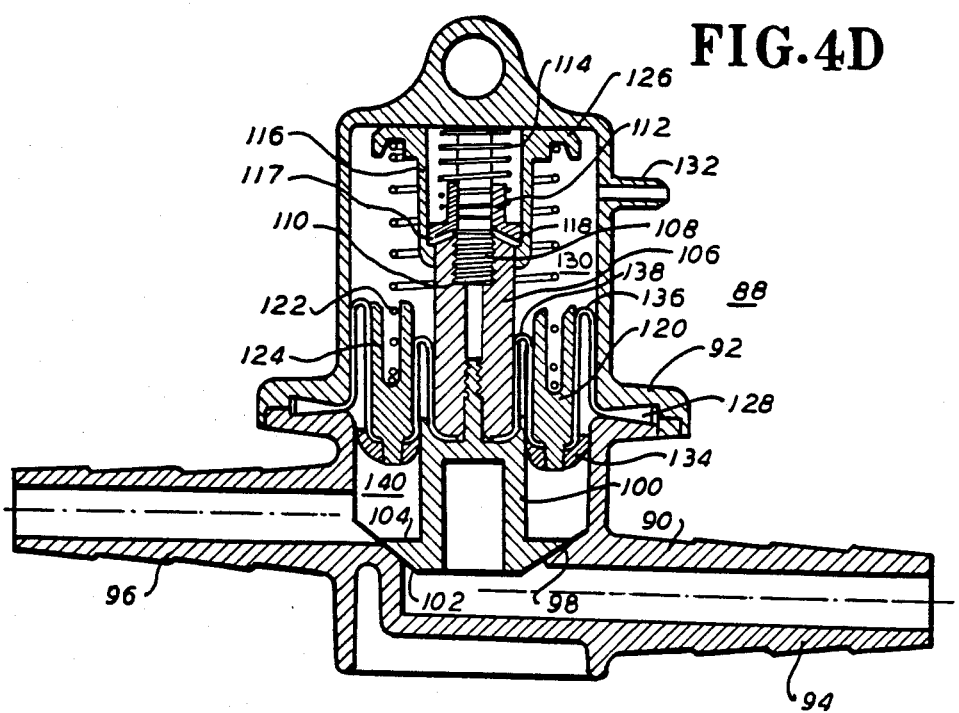
FIG. 4D is a cross-sectional view of the positive pulse device of FIG. 4A shown in the REFLUX mode.

Taking, now, the VACUUM APPLIED mode of FIG. 4B, the FIG. 4B depicts the positive pulse device 22 slightly after the control unit 12 has switched from atmospheric pressure to vacuum mode and two (2) levels of vacuum are being applied to the positive pulse device 22. Regulated vacuum is being applied to the inlet 94 and vacuum that need not be regulated, the pipeline vacuum level of the particular hospital system, is being applied to control part 132 by means of vacuum signal line 20.

Initially, as those vacuum levels are applied, the unregulated vacuum in the control chamber 130 creates a negative resultant force on the annular piston 120 since the lower surface of annular piston 120 is at or near atmospheric pressure since outlet 96 of the positive pulse device 22 is at atmospheric pressure. The moveable valve member 100 is still closed and therefore the regulated vacuum at inlet 94 does not affect that resultant force since it cannot reach outlet 96.

Accordingly, the negative resultant force on annular piston 120 causes it to move upward away from the valve seat 98 and lifts off of its contact with annular ridge 104 of moveable valve member 100. The spring bias exerted against moveable valve member 100 by large spring 122 is therefore eliminated and the moveable valve member 120 is retained in its closed position against valve seat 98 by whatever differential pressure forces exist and by means of the rather small bias exerted by small spring 108. As the annular piston 120 continues to move upward, collapsing the control chamber 130, it draws a vacuum at the outlet 96 and thus on the patient through catheter 26. A reflux chamber 140 beneath the diaphragm 128, is created and expands, separated, of course from the unregulated vacuum in the control chamber 130. Eventually, the annular piston 120 creates a sufficient vacuum at outlet 96 to approximately equal the regulated vacuum already applied to the inlet 94, and at this point, the forces acting upon the moveable valve member 100; that is, the unregulated vacuum in control chamber 130, regulated vacuum in the inlet 94, at or near regulated vacuum in outlet 96 and the small bias of small spring 108 cause the moveable valve member 100 to withdrawn from the contact with valve seat 98 and cracks that valve means between inlet 94 and outlet 96 allowing the regulated vacuum from regulated vacuum line 24 to reach the catheter 26. Thus the regulated vacuum prescribed for that particular patient is applied to the patient cavity to be drained and no higher vacuum reaches the patient despite further travel of the annular piston 120 or moveable valve member 100.

It should be noted that the position of the positive pulse device 22 shown in FIG. 4B is such that the moveable valve member 100 has merely overcome the relatively small bias of small spring 108 and thus movement of moveable valve member 100 away from valve seat 98 closes the gap 118. The moveable valve member 100 has moved approximately 0.040 inches, away from valve seat 98 sufficient to crack the valve means. Further 122 again acts to retaun the valve means closed and the cycle is completed, to be continuously repeated as the control unit 12 continues on to further cycles.

I claim:
1. A pause valve comprising a housing having an inlet for receiving a signal that changes from vacuum to atmospheric pressure and outlet for providing a signal,
  (a) a valve means in said housing intermediate said inlet and said outlet and having a valve seat and a moveable valve member adapted to move between open and closed positions with respect to said valve seat, said moveable valve member being biased towards its open position,
  (b) first and second control chambers formed on opposite sides of said moveable valve member acting upon said valve member, said first control chamber being connected to said inlet, both of said control chambers being balanced at vacuum when said received signal is a vacuum,
  (c) said first and second control chambers being fluidly connected by a restricted passage means, said restricted passage containing a reservoir,
  (d) said moveable valve member adapted to overcome said bias to close said valve responsive to the presence of atmospheric pressure in said first control chamber upon said received signal changes from vacuum to atmospheric pressure while retain- ing vacuum in said second control chamber and at said outlet,
(e) means to allow atmsopheric pressure to bleed at a predetermiined rate through said restricted passage means from said first control chamber to said second control chamber,
(f) means responsive to said second control chamber reaching atmospheric pressure balancing said control chambers to cause said bias to move said moveable valve member to the open position allowing atmospheric pressure from said inlet to reach said outlet.

2. A pause valve as defined in claim 1 wherein said restricted passage includes a fixed orifice leading to said reservoir from said first control chamber.

3. A pause valve, said pause valve having an inlet for receiving a signal changing from vacuum to atmospheric pressure and an outlet providing a changing signal from vacuum to atmospheric pressure after a predetermined time delay,
(a) said pulse valve having a valve seat between said inlet and said outlet and a moveable valve member adapted to move to open and closed positions with respect to said valve seat,
(b) first and second control chambers formed an opposite sides of said moveable valve member acting on said moveable valve member, said first and second control chambers being connected by a restricted
(c) passage means, bias adapted to move said moveable valve member to its open position when the pressures in said control chambers are equal,
(d) passage means connecting said first control chamber to said inlet,
(e) said moveable valve member adapted to move to its closed position upon the increase in pressure at said inlet by a predetermined amount to cause sufficient imbalance between said first and second control chambers to overcome said spring bias,
(f) bleed means to allow a predetermined rate of flow through said restricted passage to cause balancing of pressures in said first and second control chambers over a predetermiined period of time,
(g) said spring bias moving said moveable valve member to its open position upon said first and second control chambers reaching balanced pressures to allow the pressure in said inlet to be communicated to said outlet.

4. A pause valve as defined in claim 3 wherein said restricted passage includes a reservoir and a fixed orifice leading to said reservoir from said first control chamber.

5. A pause valve comprising a housing having an inlet for receiving a signal that changes from vacuum to atmospheric pressue and outlet for providing a signal,
(a) a valve means in said housing having a valve seat and a moveable valve member adapted to move between open and closed positions with respect to said valve seat, said moveable valve member being biased toward its open position,
(b) first and second control chambers formed on opposite sides of said moveable valve member acting upon said valve member, said first control chamber being connected to said inlet, both of said control chamber being balanced at vacuum when said received signal is at steady vacuum,
(c) said first and second control chambers being fluidly connected by a restricted passage means,
(d) said moveable valve member adapted to overcome said bias to close said valve upon the presence of atmospheric pressure in said first control chamber when said received signal changes from vacuum to atmospheric pressure while initially retaining vacuum in said second control chamber,
(e) means to allow atmospheric pressure to bleed at a predetermined rate through said restricted passage means from said first control chamber to said second control chamber,
(f) means responsive to said second chamber reaching atmospheric pressure balancing said chambers to cause said bias to move said moveable valve member to the open position allowing atmospheric pressure from said inlet to reach said outlet.

* * * * *

UNITED STATES PATENT AND TRADEMARK OFFICE
CERTIFICATE OF CORRECTION

PATENT NO. : 4,830,047
DATED : May 16, 1989
INVENTOR(S) : Colin G. Hodge

It is certified that error appears in the above-identified patent and that said Letters Patent is hereby corrected as shown below:

Col. 9, line 30, after "restricted" add --passage means,--

Col. 9, line 31, delete "passage means, bias" and insert in place thereof --spring bias means--

Signed and Sealed this

Third Day of April, 1990

*Attest:*

HARRY F. MANBECK, JR.

*Attesting Officer*  *Commissioner of Patents and Trademarks*